United States Patent [19]
Hasegawa et al.

[11] Patent Number: 5,188,962
[45] Date of Patent: Feb. 23, 1993

[54] CELL CULTIVATING APPARATUS

[75] Inventors: Yoshikazu Hasegawa, Ibaragi; Akira Hashimoto, Ryugasaki, both of Japan

[73] Assignee: Eisai Co., Ltd., Tokyo, Japan

[21] Appl. No.: 767,472

[22] Filed: Sep. 30, 1991

[30] Foreign Application Priority Data

Oct. 9, 1990 [JP] Japan .................. 2-271924

[51] Int. Cl.5 .................. C12M 3/04; C12M 3/06
[52] U.S. Cl. .................. 435/285; 435/284; 435/289; 435/311; 435/315; 210/321.67; 210/321.69
[58] Field of Search ............ 435/3, 240.242, 284–286, 435/289, 290, 291, 311, 313, 315, 316, 813, 818; 210/321.67, 321.69, 460, 463, 416.1; 417/417

[56] References Cited

U.S. PATENT DOCUMENTS

| | | | |
|---|---|---|---|
| 2,490,443 | 12/1949 | Knipper | 210/460 |
| 2,761,392 | 9/1956 | Parker | 417/417 |
| 3,460,680 | 8/1969 | Domnick | 210/460 |
| 3,606,595 | 9/1971 | Takamizawa | 417/417 |
| 4,889,812 | 12/1989 | Guinn et al. | 435/285 |
| 4,999,298 | 3/1991 | Wolfe et al. | 435/3 |

FOREIGN PATENT DOCUMENTS

| | | | |
|---|---|---|---|
| 54-06634 | 1/1979 | Japan . | |
| 1-025476 | 2/1986 | Japan | 435/284 |
| 1-219400 | 9/1989 | Japan . | |

OTHER PUBLICATIONS

Seaver, Commercial Production of Monoclonal Antibodies, N.Y., Marcel Dekker Inc., 1987, pp. 119–138.

Primary Examiner—Michael G. Wityshyn
Assistant Examiner—William H. Beisner
Attorney, Agent, or Firm—Griffin Butler Whisenhunt & Kurtossy

[57] ABSTRACT

Culture medium is circulated from a culture medium tank, through a first main duct, through a cell cultivating vessel containing therein a bundle of hollow threads, through a second main duct and back to the culture mediun tank. The first main duct is provided at an intermediate point with a vibrating columnar pump adapted to pulsate the culture medium and to vibrate outer surfaces of said hollow threads. The second main duct is provided along a tail end portion with a container serving to capture solids in the culture medium. The first main duct branches into a first sub-duct which is provided with sensors used to detect and regulate a quantity of gas mixture in the culture medium. Similarly, the second main duct branches into a second sub-duct which is provided with sensors used to detect a quantity of gas mixture in the culture medium which has been used for cell cultivation so that a level of cell metabolism occurring in the hollow threads may be detected and a flow velocity of the culture medium may be correspondingly regulated.

13 Claims, 5 Drawing Sheets

CELL CULTIVATING APPARATUS

BACKGROUND OF THE INVENTION

The present invention relates to a cell cultivating apparatus and, more particularly, to a high density cultivating system adapted to cultivate adhesive cells utilizing a cultivating apparatus containing therein a bundle of hollow threads in order that a high survivability of the cells may be maintained for a long period.

The cultivating system utilizing a cell cultivating vessel containing a bundle of hollow threads has already been disclosed, for example, by Japanese Patent Publication No. 1979-6634.

According to such prior art, the pump of a type selected from various types such as a bellows pump, a geared pump and a tubing pump is used to supply the cell cultivating vessel with culture medium from the culture medium tank, also referred to as a water tank, and there are provided in the main ducts at intermediate points along the length of these main ducts various sensors to control operation of the gas mixer and thereby to regulate quantities of respective gases mixed by said mixer.

However, such cultivating system of well known art has conventionally encountered a serious problem that the solids produced by the cells during cultivation adhere to outer surfaces of the individual hollow threads, resulting in progressive deficiency of nutriments as well as oxygen supplied to the cells. With a consequence, the number of dead cells increases with a result of excessively increasing said solid products of the cells and thus the cells perish with increasing speed.

As additional problems which have conventionally encountered by the prior art, free or floating solids are circulated in the system and often trapped by the components such as the gas mixer and the sensors, obstructing a smooth circulation and making a control of these components difficult.

SUMMARY OF THE INVENTION

In view of the problems as mentioned above, it is a principal object of the present invention to provide means adapted to allow plenty of cells present within a cell cultivating vessel to be cultivated for a long period by preventing the solids of culture medium from clinging to the bundle of hollow threads contained within said cell cultivating vessel and thus assuring the culture medium having a proper range of dissolved oxygen concentrations as well as pH values both required by the cells to be supplied to a cell cultivating tank defined within said cell cultivating vessel.

The object as set forth above is achieved, according to the present invention, by a cell cultivating apparatus including a culture medium tank, also known as a water tank, filled with culture medium, a cell cultivating vessel containing therein a bundle of hollow threads, a first main duct used to supply said cell cultivating vessel with said culture medium and a second main duct to collect said culture medium back into said water tank (culture medium tank) so that said water tank is connected by said first and second main ducts to said cell cultivating vessel, characterized by that there is provided in the first main duct a vibrating columnar pump serving to produce a pulsating flow of the culture medium within the cell cultivating vessel and thereby to vibrate outer surfaces of the respective hollow threads.

Preferably, the second main duct is provided around a tail end portion thereof with a capturing container adapted to capture solids floating in the culture medium.

It is also possible to provide a gas mixer in fluid communication with the water tank.

An arrangement is also possible without departure from the scope of the invention such that there is provided a first sub-duct branched from the first main duct and there are provided various sensors in said second sub-duct to regulate quantities of component gases to be mixed into the culture medium supplied to the cell cultivating vessel.

It is also preferable to provide a second subduct branched from the second main duct and to provide various sensors in said second sub-duct so that an effective cell cultivation can be assured by detecting quantities of the respective component gases having been mixed into the culture medium and having been used for the cell cultivation and by changing a velocity of the flow in response to a detected condition of cell metabolism occurring in the hollow threads.

According to the present invention, the flow of medium pulsates under action of the vibrating columnar pump and vibrates the hollow threads with a result that the cell cultivation lasting for along period can be easily achieved because undesirable adhesion of the solids onto the hollow threads is substantially reduced and thus clogging of the hollow threads is alleviated.

The invention allows nutrients as well as oxygen to be distributed throughout the entire cultivating tank and thereby allows plenty of cells to be cultivated at a high density.

Furthermore, the invention allows the free or floating solids to be prevented by the capturing container provided around the tail end portion of the second main duct from reentering into the first main duct and thereby solves the problem that the solids trapped not only by the hollow threads but also by the sensor might obstruct a smooth circulation and make a proper control of the respective components unreliable.

According to the invention, the gas mixer is provided directly in fluid communication with the water tank, instead of in communication with the first main duct, and controlled by the respective sensors provided in the first and second sub-ducts.

The main line comprising the first main duct and the cultivating vessel is free from any trouble which would adversely affect the cell cultivation.

BRIEF DESCRIPTION OF THE DRAWINGS

The above and other objects of the invention will be seen by reference to the description taken in connection with the accompanying drawings, in which.

DETAILED DESCRIPTION OF THE INVENTION

A preferred embodiment will be described in reference with the accompanying drawings.

Figure 1:
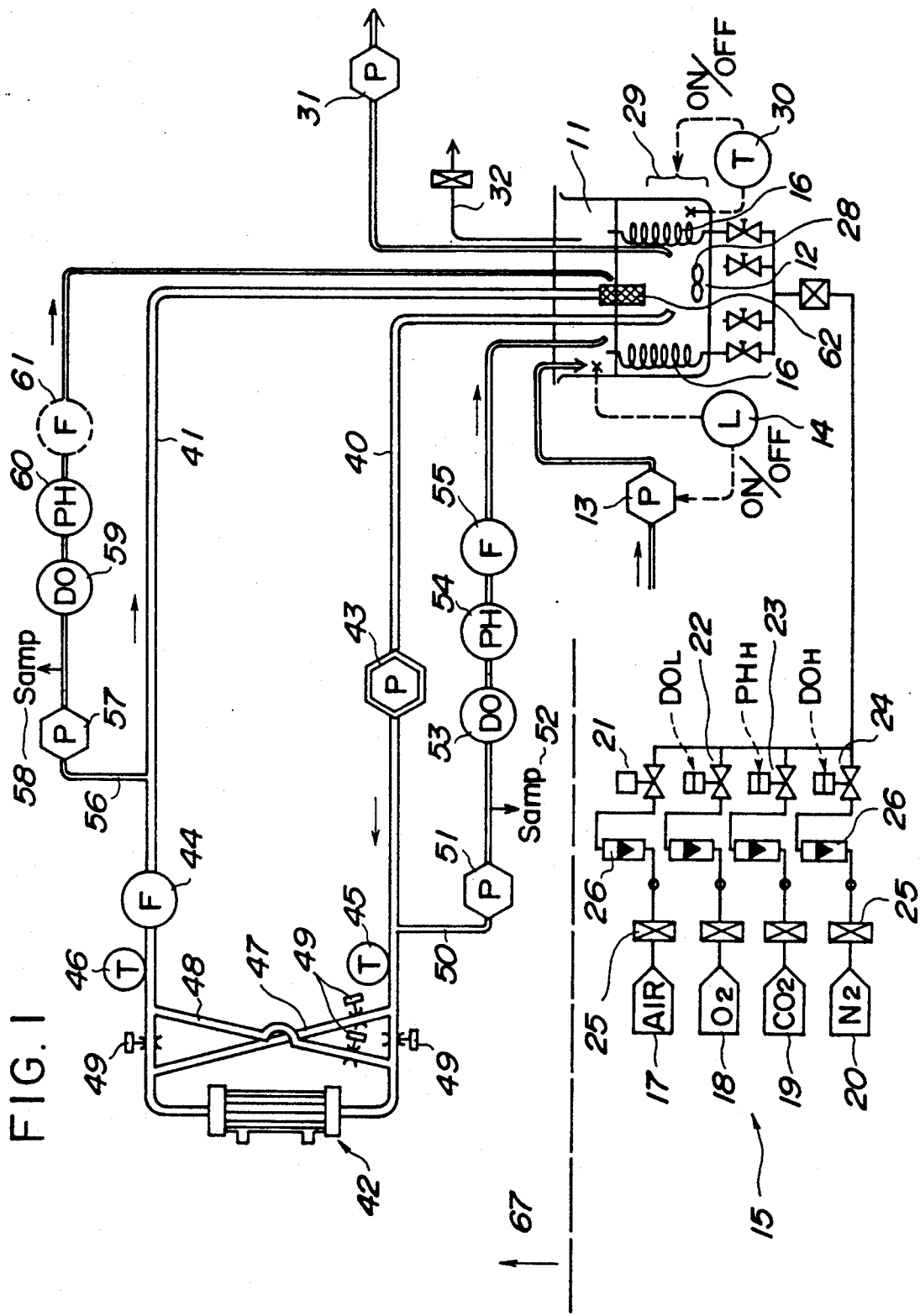
FIG. 1 is a block diagram illustrating by way of example the cell cultivating apparatus constructed in accordance with the teachings of the present invention.

FIG. 1 is a block diagram illustrating the embodiment of the cell cultivating apparatus constructed according to the teachings of the present invention. Reference numeral 11 designates a culture medium (water tank) tank filled with culture medium 12. Reference numeral 13 designates an auxiliary pump used to supply the water tank 11 with ingredients necessary for the cell cultivation and reference numeral 14 designates a level meter used to detect a level of the culture medium 12. Said auxiliary pump 13 is controlled so as to be actuated to supply the water tank 11 with said necessary ingredients when said level meter 14 detects that the level of the culture medium is lowered.

Reference numeral 15 designates a gas mixer communicating with the water tank 11 so that a gas mixture prepared within said gas mixer 15 is dissolved into the culture medium 12 through helical porous aeration pipes immersed in the water tank 11. The gas mixer 15 includes injection ports 17, 18, 19 and 20 for air, oxygen, carbon dioxide and nitrogen, respectively, and valves 21, 22, 23 and 24 provided in association with said respective component gases so that flow rates of the respective component gases are regulated by the respective valves so as to achieve a desired gas mixture ratio. The gas mixer 15 further includes filters 25 and current meters 26 provided between the respective injection ports and the valves associated with said respective injection ports.

The culture medium (water tank) tank 11 includes a stirrer 28, a heater 29 and a thermometer 30. A surplus quantity of the culture medium 12 within the water tank 11 is pumped out by a pump 31 and a surplus quantity of the respective component gases is exhausted through a duct 32.

First and second main ducts 40, 41 are connected to said water tank 11 and a cell cultivating vessel 42 is connected between said first and second main ducts 40, 41. Reference numeral 43 designates a main pump provided in the first main duct 40 at an intermediate point along the length thereof and this main pump 43 is used to pump the culture medium 12 stored in the water tank 11 into the cell cultivating vessel 42 through the first main duct 40 and to pump said culture medium 12 back to the water tank 11 through the second main duct 41. A velocity of the culture medium 12 flowing back to the water tank 11 through the second main duct 41 is detected by a current meter 44. Temperature of the culture medium 12 flowing through the first main duct 40 and the second main duct 41 are detected by thermometers 45, 46, respectively.

There are provided switching ducts 47, 48 before and behind the cell cultivating vessel 42, respectively, both connected between the first main duct 40 and the second main duct 41 so that a direction in which the culture medium 12 flows in the cell cultivating vessel 42 can be switched by actuating four valves 49 with selective combinations of opening and closing thereof.

The first main duct 40 is provided with a first sub-duct 50 branched therefrom and this first sub-duct 50 is provided, in turn, with an auxiliary pump 51, a sampling cock 52, a dissolved oxygen meter 53, a pH meter 54 and a current meter 55.

Similarly, the second main duct 41 is provided with a second sub-duct 56 branched therefrom and this sub-duct 56 is also provided with an auxiliary pump 57, a sampling cock 58, a dissolved oxygen meter 59, a pH meter 60 and a current meter 61.

Figure 2:
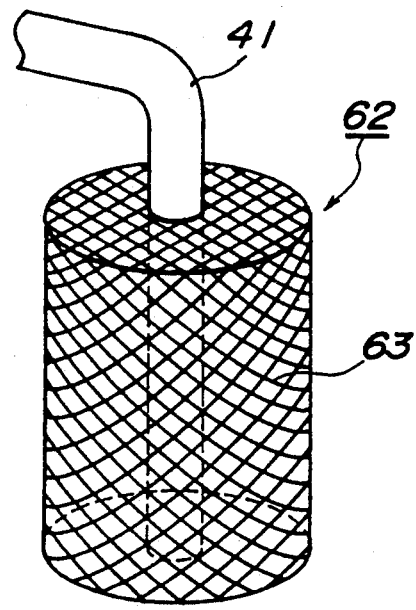
FIG. 2 and 3 are perspective and longitudinally sectional views respectively showing the capturing container provided along the tail end portion of the second main duct 41.
Figure 3:
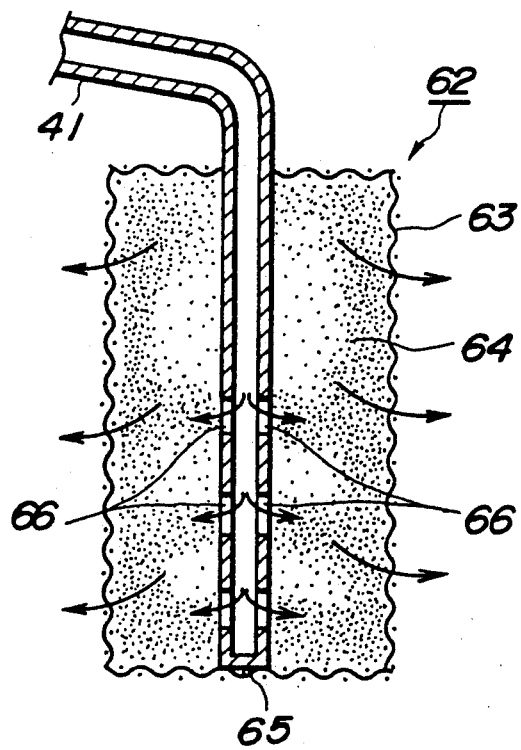

The second main duct 41 is provided around the tail end portion thereof with a capturing container 62 adapted to capture solids floating in the culture medium 12 returning to the water tank 11. The capturing container 62 has a structure as shown by FIGS. 2 and 3, i.e., comprises a basket 63 surrounding the tail end portion of the second main duct 41 and filled with heat resisting fibres 64 such as steel wool, Teflon, wool or glass wool. As will be apparent from FIG. 3, the second main duct 41 has a closed tail end 65 and the culture medium 12 flows out from the second main duct 41 through a plurality of holes 66, then is filtered by the heat resisting fibres 64 and thereafter leaves the basket 63. In this manner, the solids floating in the culture medium 12 are effectively captured by filtration through the heat resisting fibres 64.

The components including the above-mentioned cell cultivating vessel 42, the first main duct 40, the second main duct 41, the first sub-duct 50 and the second sub-duct 56 are collectively placed in a thermostatic clean bench 67 incubated at a given temperature, for example, at 37° C. under a germ-free atmosphere.

Figure 4:
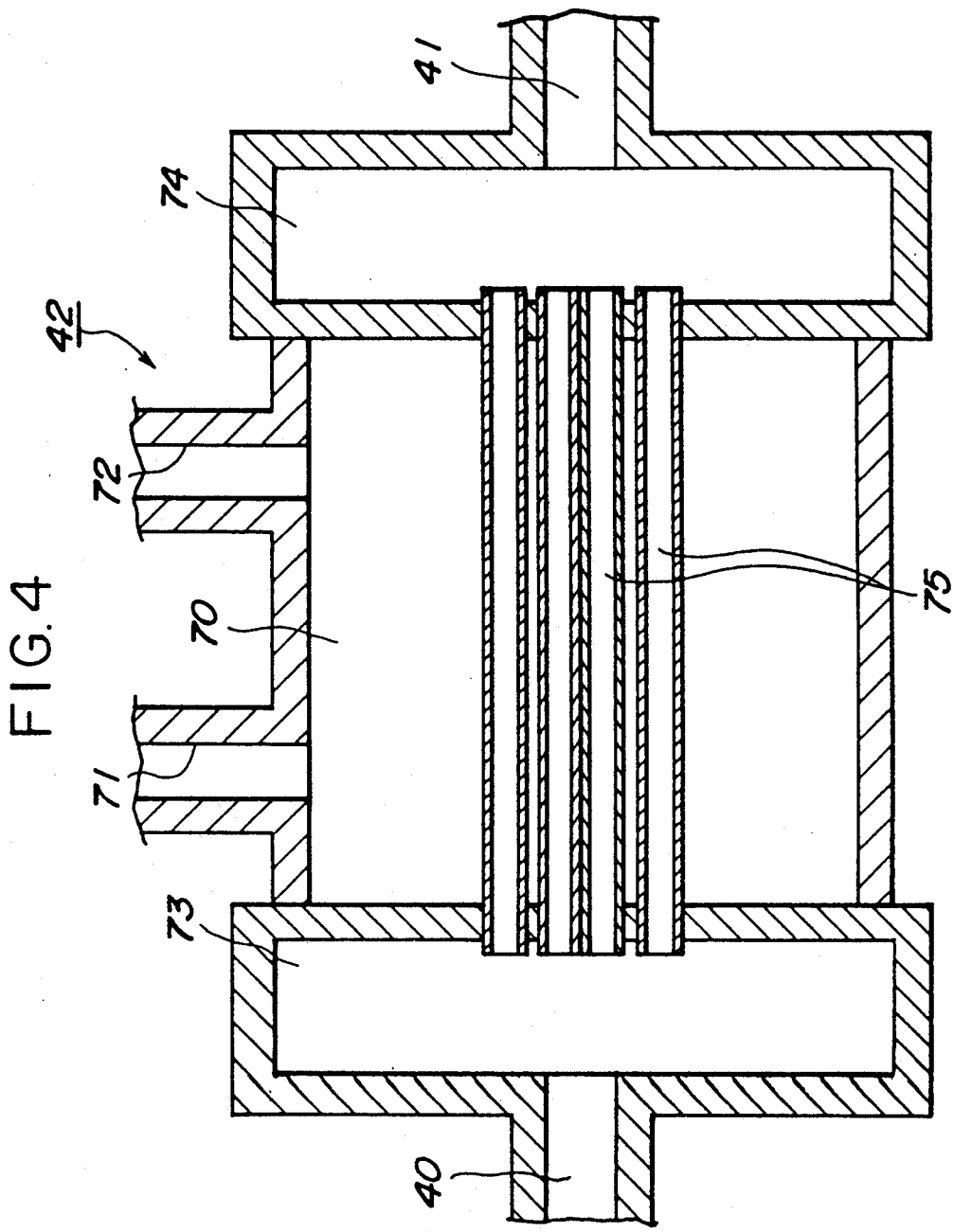
FIG. 4 is a sectional view showing the cell cultivating vessel defining the cell cultivating tank which contains therein a bundle of the hollow threads.

The cell cultivating vessel 42 is of a structure as shown by FIG. 4.

Specifically, the cell cultivating vessel 42 defines therein a cell cultivating tank 70 which is provided with inlet 71 and outlet 72 for the cells. There are provided at axially opposite sides thereof with chambers 73, 74 which communicate with each other through a plurality of hollow threads 75 axially extending within the cell cultivating tank 70 so that the cells be cultivated around these hollow threads 75.

The first main duct 40 is connected to the chamber 73 while the second main duct 41 is connected to the chamber 74.

As the culture medium 12 coming from the first main duct 40 passes through the hollow threads 75, the ingredients contained in the culture medium such as nutrients and oxygen are discharged out from the hollow threads 75 through walls thereof and thus supplied to the cells filling the cell cultivating tank 70 for the desired cultivation.

Figure 5:
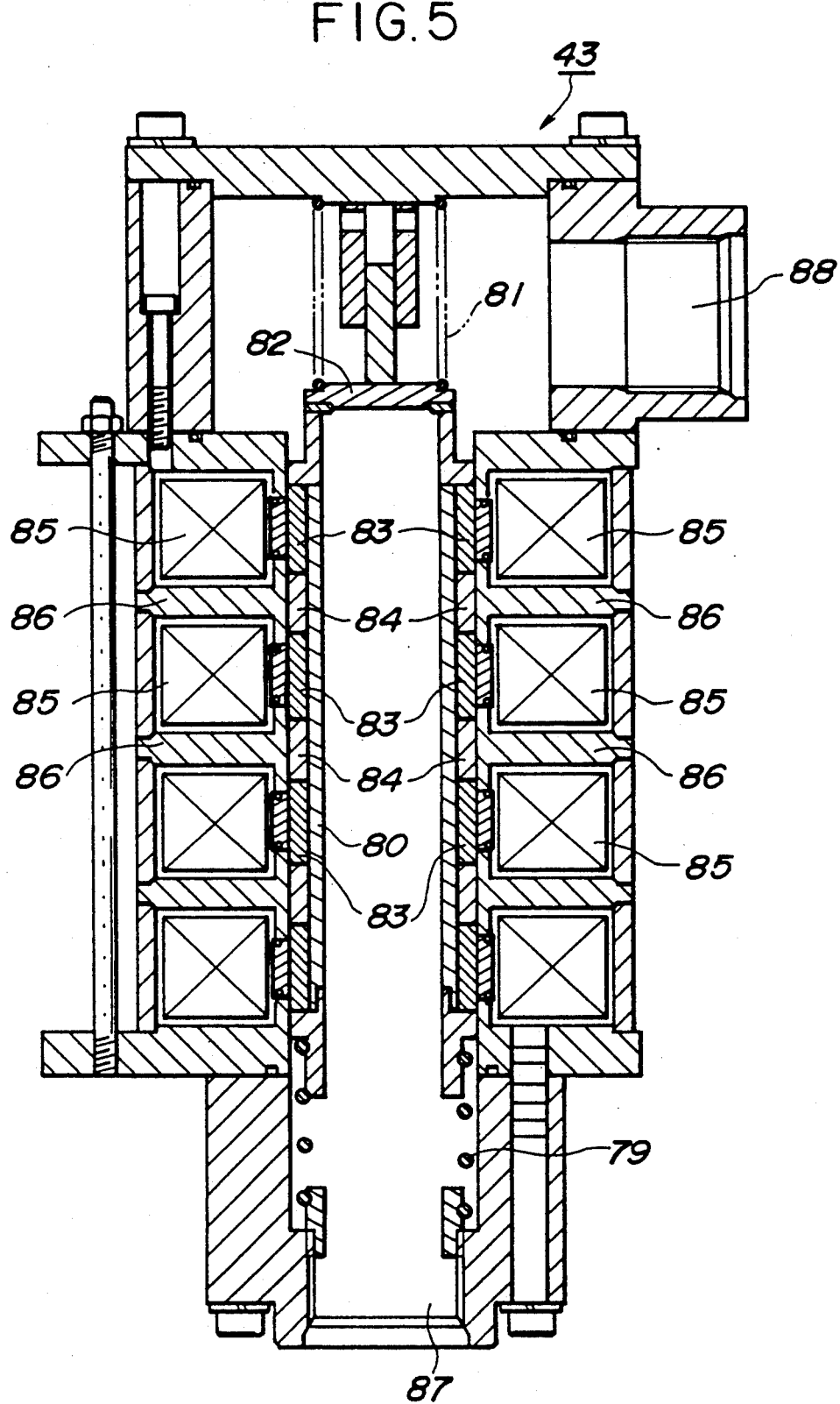
FIG. 5 is a sectional view showing the main pump in the form of a vibrating columnar pump provided in the first main duct 40.

The main pump 43 is provided in the first main duct 40 and comprises a vibrating columnar pump as shown by FIG. 5. Such vibrating columnar pump is well known, for example, from Japanese Patent Application Disclosure No. 1989-219400.

Specifically, reference numeral 80 designates a vibrating tube made of suitable magnetic material and having a lower end supported by a spring 79. A valve 82 is biased by a spring 81 downward against an upper end of said vibrating tube 80. The vibrating tube 80 is surrounded by permanent magnets 83 applied thereto so that S- and N-poles axially alternate and are axially spaced from one another by respective spacers 84.

There are provided around the vibrating tube 80 electromagnets 85 so as to be radially opposed to the associated permanent magnets 83 and these electromagnets 85 also are axially spaced from one another by respective spacers 86. With such arrangement, the vibrating tube 80 vertically vibrates when the respective electromagnets 85 are supplied with alternating current of alternately reversed directions.

Upward movement of the vibrating tube 80 causes the valve 82 to be closed, thereby causing liquid to be sucked in through a suction port 87 and downward movement of the vibrating tube 80 causes the valve 82 to be opened, thereby causing a quantity of the culture medium overflowing the top end of the vibrating tube 80 to flow out through a discharge port 88. When the vibrating columnar pump is incorporated in the first main duct 40 at the intermediate point along the length thereof so that the culture medium 12 flows from the suction port 87 to the discharge port 88 in the manner as has been described above, actuation of the said pump causes the culture medium 12 to be pulsated and circulated through the first main duct 40, the cell cultivating vessel 42 and the second main duct 41 in this order. It should be understood that the flowing velocity as well as the pulsating frequency of the culture medium 12 can be adjustably changed by regulating the magnitude and the period of the alternating current supplied to the electromagnets 85.

Now operation of the cell cultivating apparatus constructed according to the teachings of the present invention will be described.

The auxiliary pump 13 is actuated to fill the water tank 11 with the ingredients necessary for the cell cultivation and then the gas mixture made up by the gas mixer 15 is dissolved into said ingredients within the water tank 11 through the helical porous aeration pipes 16 to prepare the culture medium 12 containing the nutrients and the gas mixture both being essential for the desired cultivation. It should be noted here that the ingredients must be sometimes stored at a low temperature until they are actually supplied into the water tank 11 and it is then necessary to heat the ingredients at a given temperature utilizing the heater 29 before they are supplied into the water tank 11.

Then, the main pump 43 is actuated to circulate the culture medium 12 through the first main duct 40, the cell cultivating vessel 42 and the second main duct 41 in this order. In this manner, the cells filling the cell cultivating tank 70 defined within the cell cultivating vessel 42 are supplied with the culture medium containing the ingredients such as nutrients and oxygen which are essential for cultivation of said cells.

Factors of the culture medium such as the dissolved oxygen concentration and the pH value are adjusted to desired values by controlling the gas mixer 15 on the basis of values measured by the respective sensors provided in the first and second sub-ducts 50, 56. For example, there is provided the dissolved oxygen meter 53 in the first sub-duct 50 branched from the first main duct 40 at an intermediate point along the length of the latter and, when a value measured by said dissolved oxygen meter 53 indicates a deficiency of oxygen, the valve 22 for oxygen or the valve 21 for air is opened to prepare the gas mixture having a high oxygen content to be dissolved into the culture medium present within the water tank 11. Reversely, when an oversupply of oxygen is indicated, the valve 20 for nitrogen may be opened to increase a nitrogen content and thereby to decrease an oxygen content. In this way, a quantity of dissolved oxygen can be relatively decreased, since a total quantity of gas mixture dissolved into the culture medium is constant.

The quantity of oxygen dissolved in the culture medium 12 to be supplied to the cell cultivating tank 70 can be effectively controlled in the manner as has been described immediately above.

Regarding the culture medium 12 exiting from the cell cultivating tank 70, the second sub-duct 56 branched from the second main duct 41 at the intermediate point along the length of the latter is also provided with the dissolved oxygen meter 59 and, when a value measured by said dissolved oxygen meter 59 depending on a level of cell metabolism occurring within the hollow threads indicates a deficiency of oxygen at the outlet side, the main pump 43 may be accelerated to compensate such deficiency of oxygen.

It is also possible to calculate the current number of cells being present within the cell cultivating tank 70 by detecting the oxygen consumption from comparison of the values measured by the respective dissolved oxygen meters 53, 59.

The culture medium 12 becomes alkaline more and more as air in the gas mixture expels carbon dioxide from the culture medium and, accordingly, when the pH meter indicates unacceptably high alkalinity, the valve 23 for carbon dioxide may be opened to increase the carbon dioxide content for adjustment of pH value.

By employing the vibrating columnar pump as the main pump 43, it is possible to achieve an advantageous effect as will be described below.

As has been described in reference with FIG. 5, the culture medium 12 pulsates and flows within the cell cultivating vessel 42 as the vibrating tube 80 vertically vibrates under the effect of the alternating current. Such pulsating flow serves to vibrate the outer surfaces of the hollow threads 75 and substantially prevents the solids from clinging to these hollow threads 75 during the cultivation.

Figure 6:
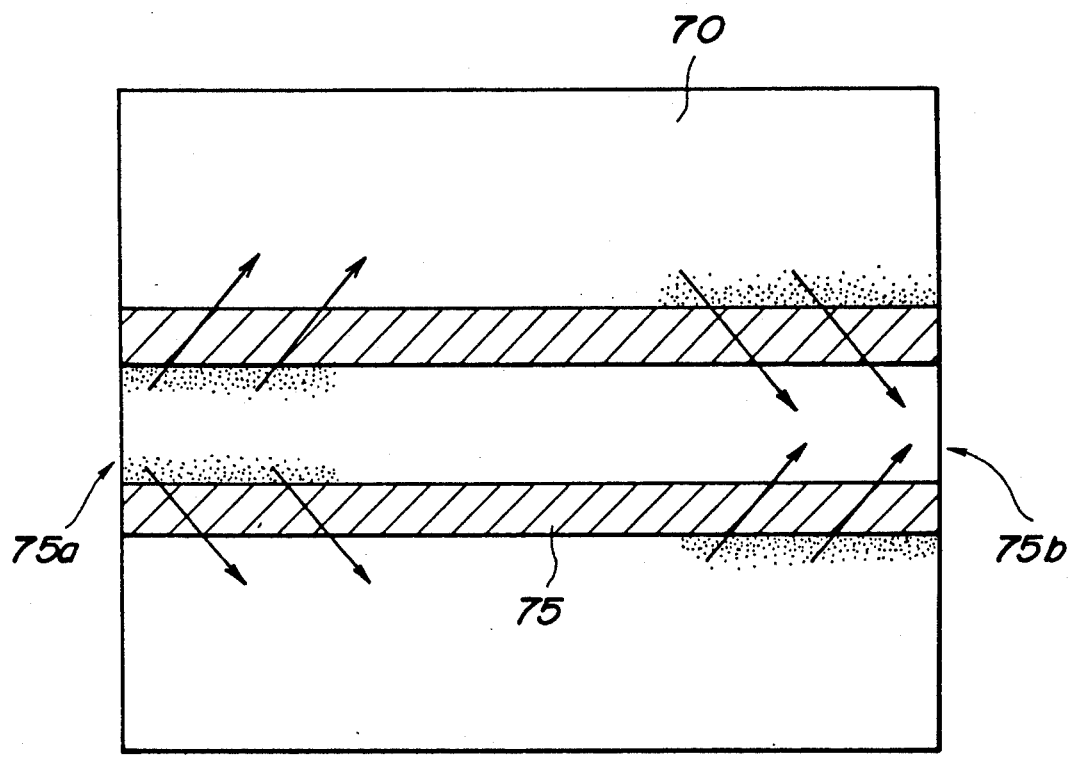
FIG. 6 is a sectional view illustrating one of the hollow threads in its non-vibrating condition.

This advantageous phenomenon will be discussed more in detail with reference to FIG. 6. With the hollow threads 75 being not vibrated, the solids produced during the cell cultivation would be apt to clog the respective hollow threads 75 along portions of these hollow threads adjacent their upstream ends 75a and apt to cling to the outer surfaces of these hollow threads 75 along portions of these hollow threads adjacent their downstream ends 75b. If such situation lasts for a long period, the nutrients contained in the culture medium 12 would not be adequately discharged from the hollow threads 75 through the walls thereof along the portions adjacent their upstream ends and lead to death of the cells due to a deficiency of the nutrients. Such situation likely occurs particularly in cultivation of the adhesive cells.

The present invention effectively avoids this situation by employing the vibrating columnar pump as the main pump 43 adapted to vibrate the outer surfaces of the hollow threads 75 and thereby to prevent the solids from clogging the respective hollow threads 75 along the portions adjacent their upstream ends and simultaneously from clinging to the outer surfaces of the hollow threads 75 along the portions adjacent their downstream ends.

The present invention allows the flowing velocity as well as the pulsating frequency of the culture medium 12 to be adjustably changed by regulating the magnitude and/or the period of the alternating current supplied to the electromagnets 85. For example, the present invention allows the flow rate to be maintained at a relatively low level for a period during which the number of cells is relatively few but the flow rate to be increased as the number of cell increases. Furthermore, the present invention allows said pulsating frequency to be optimize so as to make adhesion of the solids to the outer surfaces of the hollow threads 75 difficult.

While the invention has been particularly shown and described with reference to preferred embodiment thereof, it will be understood by those skilled in the art that the foregoing and other changes in form and details can be made therin without departing from the spirit and scope of the invention.

What is claimed is:

1. In a cell cultivating apparatus having a culture medium tank containing cell culture medium, a cell cultivating vessel having a first chamber connected to a first main duct which is in fluid communication with the culture medium tank, a second chamber connected to a second main duct which is in fluid communication with the culture medium tank, a bundle of porous, hollow threads disposed between said chambers such as to provide fluid communication between the said chambers through the hollows of the threads, and a pump for flowing the culture medium from the culture medium tank through the hollow threads and chambers and back to the culture medium tank, wherein the improvement comprises the pump being a vibrating columnar pump for pulsating the flowing culture medium sufficiently to cause vibrations of the hollow threads such that solids are substantially prevented from adhering to surfaces of the hollow threads and cell cultivation in the cell cultivating vessel is not substantially decreased, said vibrating columnar pump comprising a vibratable tube for receiving and discharging culture medium, permanent magnets disposed around said tube and electromagnets disposed near the permanent magnets such that when an alternating current is passed through the electromagnets the tube vibrates and pulses the culture medium.

2. A cell cultivating apparatus as recited in claim 1, wherein the second main duct is provided at a tail end portion thereof with a filter for filtering solids in the culture medium.

3. A cell cultivating apparatus as recited in claim 2, wherein said filter is in the form of a capturing container which comprises an opened wall basket surrounding the tail end portion and heat resisting fibers are disposed in said basket.

4. A cell cultivating apparatus as recited in claim 3, wherein the tail end portion has a closed end thereof and a plurality of holes in the tail end portion are disposed adjacent said closed end.

5. A cell cultivating apparatus as recited in claim 1, wherein there is provided a gas mixer in fluid communication with the culture medium tank to dissolve a gas mixture into said culture medium tank.

6. A cell cultivating apparatus as recited in claim 5, wherein the first main duct has a first sub-duct branched therefrom and said first sub-duct has sensors disposed therein to detect a quantity of gas mixture dissolved into the culture medium flowed to the cell cultivating vessel.

7. A cell cultivating apparatus as recited in claim 6, wherein a valve for controlling oxygen flow or a valve for controlling air flow is disposed in the gas mixer, said valve being controlled by a dissolved oxygen meter disposed in the first sub-duct, whereby the quantity of oxygen or air dissolved in the culture medium is controllable.

8. A cell cultivating apparatus as recited in claim 5, wherein the second main duct has a second sub-duct branched therefrom and said second sub-duct has sensors disposed therein to detect a quantity of gas mixture dissolved in the culture medium flowed from the cell cultivating tank.

9. A cell cultivating apparatus as recited in claim 8, wherein said sensors disposed in said second sub-duct comprise a dissolved oxygen meter to detect a quantity of dissolved oxygen in the culture medium whereby the level of cell metabolism occurring in the hollow threads is determinable and a flow velocity of the cell culture medium delivered by the pump is controlled by the dissolved oxygen meter.

10. The apparatus of claim 5, wherein the gas mixer is in fluid communication with porous aeration pipes disposed within the culture medium tank.

11. A cell cultivating apparatus as recited in claim 5, wherein a pH meter is in fluid communication with the culture medium and the pH of the culture medium is controlled by passing carbon dioxide gas through said gas mixer in response to the pH meter.

12. A cell cultivation apparatus as recited in claim 11, wherein the pH meter is disposed in a first sub-duct branched from the first main duct.

13. A cell cultivation apparatus as recited in claim 11, wherein the pH meter is disposed in a second sub-duct branched from the second main duct.

* * * * *